(12) United States Patent
Jary et al.

(10) Patent No.: US 7,371,866 B2
(45) Date of Patent: May 13, 2008

(54) PREPARATION OF AROMATIC AND HETEROAROMATIC CARBOXYLIC ACIDS BY CATALYTIC OZONOLYSIS

(75) Inventors: Walther Jary, Steinbach a. Attersee (AT); Peter Poechlauer, Linz (AT); Thorsten Ganglberger, Linz (AT)

(73) Assignee: DSM Fine Chemicals Austria Nfg GmbH & Co KG, Linz (AT)

( * ) Notice: Subject to any disclaimer, the term of this patent is extended or adjusted under 35 U.S.C. 154(b) by 773 days.

(21) Appl. No.: 10/437,994

(22) Filed: May 15, 2003

(65) Prior Publication Data

US 2003/0216577 A1 Nov. 20, 2003

(30) Foreign Application Priority Data

May 15, 2002 (AT) ................................ A 739/2002

(51) Int. Cl.
*C07D 213/80* (2006.01)
*C07D 213/803* (2006.01)
*C07D 213/807* (2006.01)
*C07C 51/265* (2006.01)

(52) U.S. Cl. ...................... 546/320; 546/327; 562/412; 562/413; 562/414; 562/415; 562/416; 562/417

(58) Field of Classification Search ................ 546/320, 546/327; 562/412, 413, 414, 415, 416, 417
See application file for complete search history.

(56) References Cited

U.S. PATENT DOCUMENTS 3,969,405 A * 7/1976 d'Ostrowick et al. ....... 562/416

FOREIGN PATENT DOCUMENTS

JP 11343283 12/1999

OTHER PUBLICATIONS

N.F. Tyupalo, Chemical Abstracts Online, CA Accession No. 95: 24981; abstract of N.F. Tyupalo, Zhurnal Prikladnoi Khimii, 54(2), 450-2 (1981).
Hay et al., J. Org. Chem, 25, 616-617 (1960).

* cited by examiner

*Primary Examiner*—Peter O'Sullivan
(74) *Attorney, Agent, or Firm*—Wenderoth, Lind & Ponack, L.L.P.

(57) ABSTRACT

A process for catalytically oxidizing alkylaromatic compounds of the formula (I)

$$Ar-CH_2-R$$

where Ar is an optionally substituted, aromatic or heteroaromatic 5-membered or 6-membered ring or a ring system having up to 20 carbon atoms where Ar may optionally be fused to a $C_1$-$C_6$-alkyl group in which up to 2 carbon atoms may be replaced by a heteroatom, and R is hydrogen, phenyl, benzyl or heteroaryl, where the phenyl, benzyl or heteroaryl radicals may also be joined to Ar by a bridge, or R together with Ar forms an optionally substituted ring system which may contain one or more optionally substituted heteroatoms, to the corresponding aromatic or heteroaromatic carboxylic acids in a solvent with ozone in the presence of a transition metal catalyst and optionally in the presence of an acid at a temperature between −70° C. and 110° C. to the corresponding carboxylic acid.

7 Claims, No Drawings

PREPARATION OF AROMATIC AND HETEROAROMATIC CARBOXYLIC ACIDS BY CATALYTIC OZONOLYSIS

Aromatic and heteroaromatic carboxylic acids, such as biphenylcarboxylic acids, bipyridylcarboxylic acids, variously substituted benzoic acids, pyridinecarboxylic acids, etc., play an important role as intermediates having particularly high added value potential in the chemical and pharmaceutical industry in various fields, such as the field of flavorings and scents, the dye, plant protection and pharmaceutical sector.

The oxidation of alkylaromatic compounds to obtain aromatic carbonyl compounds is an important reaction in organic chemistry, since it makes possible the conversion of easily accessible or obtainable organic substrates having limited reactivity to compounds having more reactive functional groups and thus having higher reactivity.

For this reason, a plurality of methods have already been suggested for oxidizing alkylaromatic compounds.

For example, J. Hanotier et al., J.C.S. Perkin II, (1972), p. 381-386 describe the oxidation of alkylaromatics in acetic acid, in the presence of oxygen and a strong acid using manganese acetate or cobalt acetate as catalyst. The yield of the desired carboxylic acids is not satisfactory. A disadvantage of this process is further that not only are the corresponding aldehydes or ketones by-produced in large percentages, but also a large proportion of the corresponding acetate and alcohol are obtained.

A. Hay et al. in J. Org. Chem. (1960); Vol 25, p. 616-617 describe the catalytic ozone-initiated oxidation using oxygen of xylenes using a cobalt catalyst in acetic acid at reflux temperature. The product obtained is the corresponding methylbenzoic acid which is further oxidized to the corresponding diacid, so that the yield of monocarboxylic acid is distinctly reduced.

Owing to the growing demand for aromatic or heteroaromatic carboxylic acids, and also owing to the various shortcomings of the existing processes, such as large percentage of by-products, temperature choice of, for example, reflux temperature, very specific catalysts, etc., it is an object of the invention to find a process which makes it possible to prepare the desired aromatic and heteroaromatic carboxylic acids in higher yields with very low by-product formation under simple process conditions.

This object is achieved, unexpectedly, by a process in which aromatic and heteroaromatic carboxylic acids are obtained by oxidizing alkylaromatic or -heteroaromatic compounds with ozone under mild reaction conditions using easily obtainable catalysts in high yield and low to negligible by-product content.

The present invention therefore provides a process for catalytically oxidizing alkylaromatic compounds of the formula (I)

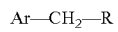

where Ar is an aromatic or heteroaromatic 5-membered or 6-membered ring or an aromatic or heteroaromatic ring system having up to 20 carbon atoms where Ar may optionally be mono- or polysubstituted by $C_1$-$C_6$-alkyl or -alkoxy, halogen, $NO_2$, CN, OH, phenyl, $NR_1R_2$ where $R_1$ and $R_2$ are each independently H or $C_1$-$C_4$-alkyl, keto groups, sulfonic acid groups, sulfonyl chloride, silyl radicals, siloxy or siloxane substituents or fused to a $C_1$-$C_6$-alkyl group in which up to 2 carbon atoms may be replaced by a heteroatom, and R is hydrogen, phenyl, benzyl or heteroaryl, and when R is phenyl, benzyl or heteroaryl, R may be joined to Ar by a bridge; or R, together with Ar, forms a ring system which is optionally substituted by $C_1$-$C_6$-alkyl or -alkoxy, halogen, $NO_2$, $NR_1R_2$ where $R_1$ and $R_2$ are each independently H or $C_1$-$C_4$-alkyl; CN, OH, phenyl, keto groups or sulfonic acid groups and may contain one or more optionally substituted heteroatoms, to the corresponding aromatic or heteroaromatic carboxylic acids, which comprises oxidizing a compound of the formula (I) in a solvent from the group of $C_1$-$C_6$-mono- or -dicarboxylic acids, esters, water, halogenated hydrocarbons, acetonitrile, $C_1$-$C_6$-alcohols, silicones, silicone oils, or chemically inert high-boiling solvents or mixtures thereof, with ozone in the presence of a transition metal catalyst and optionally in the presence of an acid at a temperature between −70° C. and 110° C. to the corresponding carboxylic acid and then isolating it from the reaction mixture.

In the process according to the invention, alkylaromatic or -heteroaromatic compounds of the formula (I) are converted to the corresponding carboxylic acids by catalytic oxidation.

The starting compounds used are compounds of the formula Ar—$CH_2$—R (I). Ar is an aromatic or heteroaromatic 5-membered or 6-membered ring or aromatic or heteroaromatic ring system having up to 20 carbon atoms. Examples include phenyl, naphthyl, anthracene, phenanthrene, indene, thiophene, pyrrole, furan, imidazole, pyridine, pyridazine, pyrimidine, pyrazine, quinoline, azepine, phenanthridine, isoquinoline, indole, dibenzothiophene, dibenzofuran, beta-carboline, indolizine, carbazole, purine, pteridine, indazole, pyrazole, 1,2,3-triazole, 1,2,4-triazole, tetrazole, oxazole, isoxazole, piperazine, dithiane, dioxane, oxazines, thiazines, pyridazines, cinnoline, phthalazine, 3,4-benzocinnoline, quinazoline, quinoxaline, phenazine, phenoxazine, phenothiazine, triazines, tetrazines, etc.

Ar is preferably phenyl, naphthyl, pyridine, imidazole and quinoline.

Ar may optionally be mono- or polysubstituted by $C_1$-$C_6$-alkyl or -alkoxy, halogen, $NO_2$, $NR_1R_2$ where $R_1$ and $R_2$ are each independently H or $C_1$-$C_4$-alkyl; CN, OH, phenyl, keto groups, sulfonic acid groups, sulfonyl chloride, siloxanes, silyl radicals, siloxy.

$C_1$-$C_6$-Alkyl or -alkoxy refer to linear or branched alkyl or alkoxy groups, such as methyl, ethyl, n-propyl, i-propyl, n-butyl, tert-butyl, methoxy, ethoxy, propoxy, butoxy, hexyloxy, etc. Preference is given to $C_1$-$C_4$-alkyl and $C_1$-$C_2$-alkoxy radicals.

Halogen is fluorine, chlorine, bromine or iodine, although preference is given to fluorine, chlorine and bromine.

$NR_1R_2$ refers to amine and substituted amines where $R_1$ and $R_2$ are each independently H or $C_1$-$C_4$-alkyl. Preferably, both radicals $R_1$ and $R_2$ are H or $C_1$-$C_2$-alkyl.

Examples of useful silyl radicals include silyl, trimethylsilyl, phenyldimethylsilyl and di-tert-butylmethylsilyl.

Ar may optionally be fused to a $C_1$-$C_6$-alkyl group in which up to 2 carbon atoms may be replaced by a heteroatom.

R may be hydrogen, phenyl, benzyl or a heteroaryl radical, such as quinolinyl, pyridyl, imidazolyl, indenyl or furanyl.

In the case that R is phenyl, benzyl or a heteroaryl radical, R may also be joined to Ar by a $C_2$-$C_8$-alkyl radical bridge.

R together with Ar may also form a ring system which is optionally substituted by $C_1$-$C_6$-alkyl or -alkoxy, halogen, $NO_2$, $NR_1R_2$ where $R_1$ and $R_2$ are each independently H or $C_1$-$C_4$-alkyl; CN, OH, phenyl, keto groups or sulfonic acid groups and may contain one or more optionally substituted heteroatoms.

If necessary, the substituents may be protected by suitable protecting groups known from the prior art.

Examples of compounds of the formula (I) include toluene, 2-bromotoluene, 3-bromotoluene, 4-bromotoluene, 2-chlorotoluene, 3-chlorotoluene, 4-chlorotoluene, 2-fluorotoluene, 3-fluorotoluene, 4-fluorotoluene, 3,4-dichlorotoluene, 3,4-difluorotoluene, 4-tert-butyltoluene, ethylbenzene, o-nitrotoluene, m-nitrotoluene, p-trifluoromethyltoluene, 3,5-di(trifluoromethyl)toluene, p-nitrotoluene, p-toluidine, p-cumene, cresols, mono-, di- or trialkyl- or -alkoxynapthalenes such as methylnaphthalene and methoxynaphthalene, methylanthracene, diphenylmethane, p-toluenesulfonyl chloride, 2-methylpyridine, 3-methylpyridine, 4-methylpyridine, 2,3-dimethylpyridine, 2,4-dimethylpyridine, 2,5-dimethylpyridine, 2,6-dimethylpyridine, 3,5-di-tert-butyl-4-hydroxytoluene, 3,4-dimethoxytoluene, 2,3-dihydroxytoluene, 3,4,5-trimethoxytoluene, 2-hydroxy-5-nitrotoluene, 3,4-dihydroxy-5-nitrotoluene, 4-cyanotoluene, 2-(p-tolyl)pyridine, 4-(p-tolyl)pyridine, biphenyls, bipyridyls, etc.

The catalytic oxidation according to the invention is effected in a solvent from the group of $C_1$-$C_6$-mono- or -dicarboxylic acids, esters, water, halogenated hydrocarbons, silicones, silicone oils, chemically inert high-boiling solvents, acetonitrile, acetone or $C_1$-$C_6$-alcohols.

Suitable solvents are therefore $C_1$-$C_6$-mono- or -dicarboxylic acids, such as acetic acid, propionic acid, butyric acid, etc., and also solutions of carboxylic acids in other solvents.

The esters used are preferably $C_1$-$C_6$-carboxylic esters, such as ethyl acetate, isopropyl acetate, t-butyl acetate or n-butyl acetate.

Examples of suitable halogenated hydrocarbons include dichloromethane, 1,2-dichloroethane, chloroform or carbon tetrachloride.

Also suitable are $C_1$-$C_6$-alcohols, such as methanol, n-butanol, tert-butanol, silicones and silicone oils and chemically inert high-boiling solvents, for example white oil.

The abovementioned solvents may also be used as mixtures.

Preference is given to using $C_1$-$C_4$-mono- or -dicarboxylic acids such as acetic acid, propionic acid or butyric acid, or $C_1$-$C_4$-alcohols such as methanol, n-butanol or tert-butanol; or mixtures with water or chlorinated hydrocarbons.

Particularly preferred solvents are acetic acid, or mixtures of acetic acid in water or only water.

The catalysts used are transition metal catalysts. Suitable transition metal catalysts are based on elements from groups 3B such as Sc, Y, La, Ce, Sm or lanthanides, Ac or other actinides, from group 4B (Ti, Zr, Hf), group 5B (V, Nb, Ta), group 6B (Cr, Mo, W), group 7B (Mn, Tc, Re), group 8 (Fe, Ru, Os, Co, Rh, Ir, Ni, Pd, Pt), or group 1B (Cu, Ag, Au).

Preference is given to using catalysts which contain Sc, Sm or Y from group 3B, La or Ce from the lanthanide group; Ti or Zr from group 4B, V or Ta from group 5B, Cr, Mo or W from group 6B, Mn or Re from group 7B, Fe, Co, Ni or Pd from group 8B or Cu from group 1B.

Particular preference is given to catalysts which contain Sm, La, Ce, Ni, Co, V, Cr, Fe, Mn or Cu.

The catalyst may be used as a metal hydroxide, metal oxide, as an organic salt, inorganic salt, etc.

Examples of hydroxides include $Mn(OH)_2$, $MnO(OH)_2$, $Fe(OH)_2$ and $Fe(OH)_3$. Examples of suitable oxides include $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $Cu_2O_3$, etc.

Examples of organic salts include formates, acetates, propionates, acetylacetonates, benzoates, alkoxides, naphthenates, stearates and other salts with $C_2$-$C_{20}$ fatty acids of Co, Mn, Ce, Ti, Zr, V, Cr, Mo, Fe, Ru, Ni, Pd, Cu, etc.

Examples of inorganic salts include nitrates, sulfates, phosphates, carbonates and halides of V, Co, Fe, Mn, Ni, Cu, etc.

The catalyst may also be used in the form of a complex, for instance as described in EP-A1-0 824 962, as a divalent catalyst, with ligands or bridged, etc.

Preference is given to using the catalyst as an organic salt, for example acetate, acetylacetonate, picolinate, citrate, neocuproine, etc., and also as an inorganic salt, for example nitrate, etc.

The catalyst may, if desired, be applied in solid form to a support. Examples of suitable supports include silica, zeolite, activated carbon, etc., or other porous supports. It is also possible in the process according to the invention to use catalyst mixtures of two or more catalysts.

In the process according to the invention, the catalyst or catalyst mixture is used in an amount of from 0.001 mol % to 1 mol %, preferably from 0.01 to 1 mol % and more preferably from 0.1 to 0.25% mol %, per mole of substrate.

The catalytic oxidation is effected optionally in the presence of an acid. Useful acids are strong acids, such as $H_2SO_4$, $H_2SO_4/SO_3$, $HNO_3$ and also other mineral acids or trichloroacetic acid, trifluoroacetic acid, methanesulfonic acid or other sulfonic acids.

Preference is given to carrying out the process according to the invention in the presence of an acid, and particular preference is given to using $H_2SO_4$ as the acid.

The amount of added acid is from 0.001 mol to 1 mol, preferably from 0.01 to 0.8 mol and more preferably from 0.1 to 0.5 mol, per mole of substrate.

Ozone serves as the oxidizing agent. Preference is given to using ozone in about double the equimolar amount, based on the substrate. However, it is also possible to use an excess of ozone.

The reaction temperature in the process according to the invention is between −70 and +110° C., preferably between −20 and 70° C. and more preferably between 0 and 30° C.

In the process according to the invention, the substrate, the catalyst and any acid are initially charged in the appropriate solvent and brought to the desired reaction temperature. Ozone is then introduced into the reaction mixture until the ozonolysis is complete. Any excess ozone remaining in the solvent is blown out using nitrogen.

The reaction product is then isolated, depending on its aggregate state, by customary methods, such as extraction, distillation, chromatography, etc. in the case of liquid products, or filtration, centrifugation, sublimation, etc. in the case of solid products.

The process according to the invention allows the desired aromatic and heteroaromatic carboxylic acids to be obtained in a simple manner in high yields with a distinctly lower by-product fraction compared to the prior art. The process according to the invention is particularly suitable for preparing substituted benzoic acids, pyridinecarboxylic acids, naphthalenecarboxylic acids or other heteroaromatic carboxylic acids.

Examples of carboxylic acids which may advantageously be prepared according to the invention include: 2-bromobenzoic acid, 3-bromobenzoic acid, 4-bromobenzoic acid, 2,3-dibromobenzoic acid, 2,4-dibromobenzoic acid, 2,6-dibromobenzoic acid, 3,4-dibromobenzoic acid, 3,5-dibromobenzoic acid, 2,4,6-tribromobenzoic acid, 2,3,5-tribromobenzoic acid, 2,3,6-tribromobenzoic acid, 2-fluorobenzoic acid, 3-fluorobenzoic acid, 4-fluorobenzoic acid, 2,3-difluorobenzoic acid, 2,4-difluorobenzoic acid, 2,6-difluorobenzoic acid, 3,4-difluorobenzoic acid, 3,5-difluorobenzoic acid, 2,4,6-trifluorobenzoic acid, 2,3,5-trifluorobenzoic acid, 2,3,6-trifluorobenzoic acid, 2-chlorobenzoic acid, 3-chlorobenzoic acid, 4-chlorobenzoic acid, 2,3-dichlorobenzoic acid, 2,4-dichlorobenzoic acid, 2,6-dichlorobenzoic acid, 3,4-dichlorobenzoic acid, 3,5-dichlorobenzoic acid, 2,4,6-trichlorobenzoic acid, 2,6-dichlorobenzoic acid, 2,3,5-trichlorobenzoic acid, 2,3,6-trichlorobenzoic acid, 2-iodobenzoic acid, 3-iodobenzoic acid, 4-iodobenzoic acid, 2,3-diiodobenzoic acid, 2,4-diiodobenzoic acid, 2,6-diiodobenzoic acid, 3,4-diiodobenzoic acid, 3,5-diiodobenzoic acid, 2,4,6-triiodobenzoic acid, 2,6-diiodobenzoic acid, 2,3,5-triiodobenzoic acid, 2,3,6-triiodobenzoic acid, 2-methoxybenzoic acid, 3-methoxybenzoic acid, 4-methoxybenzoic acid, 2,3-dimethoxybenzoic acid, 2,4-dimethoxybenzoic acid, 2,6-dimethoxybenzoic acid, 3,4-dimethoxybenzoic acid, 3,5-dimethoxybenzoic acid, 2,4,6-dimethoxybenzoic acid, 2,6-dimethoxybenzoic acid, 2,3,5-trimethoxybenzoic acid, 2,3,6-trimethoxybenzoic acid, 2-ethoxybenzoic acid, 3-ethoxybenzoic acid, 4-ethoxybenzoic acid, 2,3-diethoxybenzoic acid, 2,4-diethoxybenzoic acid, 2,6-diethoxybenzoic acid, 3,4-diethoxybenzoic acid, 3,5-diethoxybenzoic acid, 2,4,6-triethoxybenzoic acid, 2,3,5-triethoxybenzoic acid, 2,3,6-triethoxybenzoic acid, 2-nitrobenzoic acid, 3-nitrobenzoic acid, 4-nitrobenzoic acid, 2,3-dinitrobenzoic acid, 2,4-dinitrobenzoic acid, 2,6-dinitrobenzoic acid, 3,4-dinitrobenzoic acid, 3,5-dinitrobenzoic acid, 2,4,6-trinitrobenzoic acid, 2,3,5-trinitrobenzoic acid, 2,3,6-trinitrobenzoic acid, 2-cyanobenzoic acid, 3-cyanobenzoic acid, 4-cyanobenzoic acid, 2,3-dicyanobenzoic acid, 2,4-dicyanobenzoic acid, 2,6-dicyanobenzoic acid, 3,4-dicyanobenzoic acid, 3,5-dicyanobenzoic acid, 2,4,6-tricyanobenzoic acid, 2,3,5-tricyanobenzoic acid, 2,3,6-tricyanobenzoic acid, 2-trifluoromethylbenzoic acid, 3-trifluoromethylbenzoic acid, 4-trifluoromethylbenzoic acid, 2,3-di(trifluoromethyl)benzoic acid, 2,4-di(trifluoromethyl)benzoic acid, 2,6-di(trifluoromethyl)benzoic acid, 3,4-di(trifluoromethyl)benzoic acid, 3,5-di(trifluoromethyl)benzoic acid, 2,4,6-tri(trifluoromethyl)benzoic acid, 2,3,5-tri(trifluoromethyl)benzoic acid, 2,3,6-tri(trifluoromethyl)benzoic acid, 2-methylbenzoic acid, 3-methylbenzoic acid, 4-methylbenzoic acid, 2,3-dimethylbenzoic acid, 2,4-dimethylbenzoic acid, 2,6-dimethylbenzoic acid, 3,4-dimethylbenzoic acid, 3,5-dimethylbenzoic acid, 2,4,6-trimethylbenzoic acid, 2,3,5-trimethylbenzoic acid, 2,3,6-trimethylbenzoic acid, 2-ethylbenzoic acid, 3-ethylbenzoic acid, 4-ethylbenzoic acid, 2,3-diethylbenzoic acid, 2,4-diethylbenzoic acid, 2,6-diethylbenzoic acid, 3,4-diethylbenzoic acid, 3,5-diethylbenzoic acid, 2,4,6-triethylbenzoic acid, 2,3,5-triethylbenzoic acid, 2,3,6-triethylbenzoic acid, 2-aminobenzoic acid, 3-aminobenzoic acid, 4-aminobenzoic acid, 2,3-diaminobenzoic acid, 2,4-diaminobenzoic acid, 2,6-diaminobenzoic acid, 3,4-diaminobenzoic acid, 3,5-diaminobenzoic acid, 2,4,6-triaminobenzoic acid, 2,3,5-triaminobenzoic acid, 2,3,6-triaminobenzoic acid, 4-tert-butylbenzoic acid, 3-tert-butylbenzoic acid, 3,5-di-tert-butylbenzoic acid, 4-hydroxy-3,5-di-tert-butylbenzoic acid, 4-fluoro-3,5-di-tert-butylbenzoic acid, 2-chloro-4-tert-butylbenzoic acid, 2-fluorodi-tert-butylbenzoic acid, 4-hydroxy-3,5-dinitrobenzoic acid, 4-fluoro-3,5-dinitrobenzoic acid, 2-chloro-4-nitrobenzoic acid, 2-fluorodinitrobenzoic acid, 2-hydroxy-5-nitrobenzoic acid, 3-nitro-5-trifluoromethylbenzoic acid, 4-hydroxy-3,5-dibromobenzoic acid, 4-fluoro-3,5-dibromobenzoic acid, 2-chloro-4-bromobenzoic acid, 2-fluorodibromobenzoic acid, 2-hydroxy-5-bromobenzoic acid, 3-bromo-5-trifluoromethylbenzoic acid, 4-hydroxy-3,5-dichlorobenzoic acid, 4-fluoro-3,5-dichlorobenzoic acid, 2-fluorodichlorobenzoic acid, 2-hydroxy-5-chlorobenzoic acid, 3-chloro-5-trifluoromethylbenzoic acid, 4-hydroxy-3,5-difluorobenzoic acid, 2-chloro-4-fluorobenzoic acid, 2-hydroxy-5-fluorobenzoic acid, 3-fluoro-5-trifluoromethylbenzoic acid, 4-(2-pyridyl)benzoic acid, 4-(4-pyridyl)benzoic acid, 2-pyridinecarboxylic acid, 3-pyridinecarboxylic acid, 4-pyridinecarboxylic acid, etc.

EXAMPLE 1

4-Bromobenzoic acid

In a 100 ml jacketed vessel, 200 ml of acetic acid, 0.24 g (0.98 mmol) of manganese(II) acetate, 9.8 g (0.1 mol) of sulfuric acid and 34.1 g (0.2 mol) of 4-bromotoluene were initially charged. The mixture was cooled to 16° C. and 20.0 g (0.41 mol) of ozone were introduced within a period of 75 minutes. After completion of ozonolysis, the ozone present in the solvent was blown out using nitrogen.

Analysis of the reaction mixture by means of HPLC or GC gave the following results: 4-bromotoluene: <0.1%; 4-bromobenzoic acid: 98%

EXAMPLE 2

4-Bromobenzoic acid

In a 100 ml jacketed vessel, 200 ml of acetic acid, 0.24 g (0.89 mmol) of manganese(II) acetate, and 34.1 g (0.2 mmol) of 4-bromotoluene were initially charged. The mixture was cooled to 16° C. and 20.0 g (0.41 mol) of ozone were introduced within a period of 100 minutes. After completion of ozonolysis, the ozone present in the solvent was blown out using nitrogen.

Analysis of the reaction mixture by means of HPLC or GC gave the following results: 4-bromotoluene: <0.1%; 4-bromobenzoic acid: 98%

EXAMPLE 3

4-tert-Butylbenzoic acid

In a 100 ml jacketed vessel, 200 ml of acetic acid, 0.24 g of manganese(II) acetate, 9.8 g of sulfuric acid and 14.8 g of 4-tert-butyltoluene were initially charged. The mixture was cooled to 16° C. and 10.5 g of ozone were introduced within a period of 100 minutes. After completion of ozonolysis, the ozone present in the solvent was blown out using nitrogen.

Analysis of the reaction mixture by means of HPLC or GC gave the following results: 4-tert-butyltoluene: <0.1%; 4-tert-butylbenzoic acid: 98%

EXAMPLE 4

3,4-Dichlorobenzoic acid

In a 100 ml jacketed vessel, 200 ml of acetic acid, 0.24 g of manganese(II) acetate, 9.8 g of sulfuric acid and 34.5 g of 3,4-dichlorotoluene were initially charged. The mixture was cooled to 16° C. and 20 g of ozone were introduced within a period of 175 minutes. After completion of ozonolysis, the ozone present in the solvent was blown out using nitrogen.

Analysis of the reaction mixture by means of HPLC or GC gave the following results: 3,4-dichlorotoluene: <0.1%; 3,4-dichlorobenzoic acid: 96%

EXAMPLE 5

3,4-Difluorobenzoic acid

In a 100 ml jacketed vessel, 200 ml of acetic acid, 0.05 g of manganese(II) acetate, 1.91 g of sulfuric acid and 14.1 g of 3,4-difluorotoluene were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 3,4-difluorotoluene: <0.1%; 3,4-difluorobenzoic acid: 98%

EXAMPLE 6

3-Chlorobenzoic acid

In a 100 ml jacketed vessel, 200 ml of acetic acid, 0.08 g of cerium(III) acetate, 4.9 g of sulfuric acid and 12.65 g of 3-chlorotoluene were initially charged. The mixture was cooled to 16° C. and 5.15 g of ozone were introduced within a period of 75 minutes. After completion of ozonolysis, the ozone present in the solvent was blown out using nitrogen.

Analysis of the reaction mixture by means of HPLC or GC gave the following results: 3-chlorotoluene: <0.1%; 3-chlorobenzoic acid: 98%

EXAMPLE 7

2-Pyridinecarboxylic acid

In a 100 ml jacketed vessel, 200 ml of acetic acid, 0.05 g of manganese(II) acetate, 1.91 g of sulfuric acid and 14.1 g of 2-methylpyridine were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 2-methylpyridine: <0.1%; 2-pyridinecarboxylic acid: 97%

EXAMPLE 8

3-Pyridinecarboxylic acid

In a 100 ml jacketed vessel, 200 ml of acetic acid, 0.05 g of manganese(II) acetate, 1.91 g of sulfuric acid and 14.1 g of 3-methylpyridine were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 3-methylpyridine: <0.1%; 3-pyridinecarboxylic acid: 96-98%

EXAMPLE 9

4-Pyridinecarboxylic acid

In a 100 ml jacketed vessel, 200 ml of acetic acid, 0.05 g of manganese(II) acetate, 1.91 g of sulfuric acid and 14.1 g of 4-methylpyridine were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 4-methylpyridine: <0.1%; 4-pyridinecarboxylic acid: 97%

EXAMPLE 10

4-(2-Pyridyl)benzoic acid

In a 100 ml jacketed vessel, 200 ml of acetic acid, 0.05 g of manganese(II) acetate, 1.74 g of sulfuric acid and 3.0 g of 2-(p-tolyl)pyridine were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 2-(p-tolyl)pyridine: <0.1%; 4-(2-pyridyl)benzoic acid: 94-97%

EXAMPLE 11

4-(4-Pyridyl)benzoic acid

In a 100 ml jacketed vessel, 200 ml of acetic acid, 0.05 g of manganese(II) acetate, 1.74 g of sulfuric acid and 3.0 g of 4-(p-tolyl)pyridine were initially charged. The mixture was cooled to 16° C. and 4.0 g of ozone were introduced within a period of 60 minutes. After completion of ozonolysis, the ozone present in the solvent was blown out using nitrogen.

Analysis of the reaction mixture by means of HPLC or GC gave the following results: 4-(p-tolyl)pyridine: <0.1%; 4-(4-pyridyl)benzoic acid: 94-97%

What is claimed is:

1. A process for catalytically oxidizing alkylaromatic compounds of the formula (I)

Ar—CH$_3$ where Ar is an aromatic or heteroaromatic 5-membered or 6-membered ring or an aromatic or heteroaromatic ring system having up to 20 carbon atoms where Ar may optionally be mono- or polysubstituted by $C_1$-$C_6$-alkyl or -alkoxy, halogen, $NO_2$, $NR_1R_2$ where $R_1$ and $R_2$ are each independently H or $C_1$-$C_4$-alkyl, CN, OH, phenyl, keto groups, sulfonic acid groups, sulfonyl chloride, silyl radicals, siloxy or siloxane substituents or fused to a $C_1$-$C_6$-alkyl group in which up to 2 carbon atoms may be replaced by a heteroatom, to the corresponding aromatic or heteroaromatic carboxylic acids, which comprises oxidizing a compound of the formula (I) in a solvent from the group of $C_1$-$C_6$-mono- or -dicarboxylic acids, esters, water, halogenated hydrocarbons, acetonitrile, $C_1$-$C_6$-alcohols, silicones, silicone oils, or chemically inert high-boiling solvents or mixtures thereof, with ozone in the presence of a transition metal catalyst and optionally in the presence of an acid at a temperature between −20° C. and 30° C. to the corresponding carboxylic acid and then isolating it from the reaction mixture.

2. The process as claimed in claim 1, wherein Ar in the formula (I) is a phenyl, naphthyl, anthracene, pyridine, imidazole or quinoline ring or ring system which may optionally be mono- or polysubstituted by $C_1$-$C_4$-alkyl, $C_1$-$C_2$-alkoxy, fluorine, chlorine, bromine, iodine, $NO_2$, OH, CN, phenyl or $NH_2$, or fused to a $C_4$-alkyl group in which two carbon atoms may optionally be replaced by O.

3. The process as claimed in claim 1, wherein the solvent used is acetic acid, propionic acid, butyric acid, methanol, n-butanol, tert-butanol or a mixture with water or a chlorinated hydrocarbon.

4. The process as claimed in claim 1, wherein the transition metal catalyst used is a catalyst based on one of the elements Sc, Sm or Y from group 3B, La or Ce from the lanthanide group; Ti or Zr from group 4B, V or Ta from group 5B, Cr, Mo or W from group 6B, Mn or Re from group 7B, Fe, Co, Ni or Pd from group 8B or Cu from group 1B, in the form of an organic or inorganic salt, or a mixture of the same.

5. The process as claimed in claim 1, wherein the catalytic oxidation is carried out in the presence of a strong acid from the group of $H_2SO_4$, $H_2SO_4/SO_3$, $HNO_3$, trichioroacetic acid, trifluoroacetic acid or methanesulfonic acid.

6. The process as claimed in claim 1 wherein ozone is used in a double equimolar amount based on the substrate.

7. The process as claimed in claim 1, wherein any ozone remaining in the solvent after completion of ozonolysis is blown out using nitrogen and the carboxylic acid is isolated from the reaction mixture, depending on the aggregate state, by extraction, distillation, chromatography, filtration, centrifugation or sublimation.

\* \* \* \* \*